United States Patent [19]

Adams et al.

[11] Patent Number: 4,589,420
[45] Date of Patent: May 20, 1986

[54] METHOD AND APPARATUS FOR ECG RHYTHM ANALYSIS

[75] Inventors: Isabelle M. Adams, Woodland Hills; James M. Carlson, Chatsworth; James B. Rooks, Canyon Country; Amalia Yeshaya, Los Angeles, all of Calif.

[73] Assignee: Spacelabs Inc., Chatsworth, Calif.

[21] Appl. No.: 630,782

[22] Filed: Jul. 13, 1984

[51] Int. Cl.⁴ ............................................. A61B 5/04
[52] U.S. Cl. ................................................. 128/702
[58] Field of Search ..................... 128/696, 702–706, 128/708, 710; 364/415, 417

[56] References Cited

U.S. PATENT DOCUMENTS

| | | |
|---|---|---|
| 3,215,136 | 11/1965 | Holter et al. |
| 3,554,187 | 1/1971 | Glassner et al. ................. 128/706 |
| 3,759,248 | 9/1973 | Valiquette . |
| 3,807,392 | 4/1974 | Harris ................................. 128/702 |
| 3,832,994 | 9/1974 | Bicher et al. ....................... 128/705 |
| 3,940,692 | 2/1976 | Neilson ............................... 128/702 |
| 4,023,564 | 5/1977 | Valiquette . |
| 4,231,374 | 11/1980 | Hudek et al. ...................... 128/702 |
| 4,250,888 | 2/1981 | Grosskopf .......................... 128/706 |
| 4,336,810 | 6/1982 | Anderson et al. . |
| 4,360,030 | 11/1982 | Citron et al. . |
| 4,417,306 | 11/1983 | Citron et al. . |

FOREIGN PATENT DOCUMENTS

721079  3/1980  U.S.S.R. .............................. 128/703

OTHER PUBLICATIONS

Bonner et al "Computer Diagnosis of Electrocardiograms. 11. A Computer Program for EKG Measurements" *Comp and Biomed Res*, vol. 1, 1968, pp. 366–386.

Primary Examiner—William E. Kamm
Assistant Examiner—Mitchell J. Shein
Attorney, Agent, or Firm—Lawrence S. Levinson; Robert E. Lee, Jr.

[57] ABSTRACT

A method and apparatus for automatic rhythm analysis of digitized ECG signals. Candidate heartbeats are detected and the noise of the ECG signal portion containing the candidate is evaluated to determine whether the candidate is a valid nominal or noisy beat or an invalid noisy saturated signal. The timing of detected heartbeats, both noisy and nominal, are determined relative to prior validated heartbeats. Features of the detected heartbeats are automatically extracted including onset, offset and R wave locations; QRS complex width; R-R interval based on the onset points; instantaneous and averaged heartrates; and others. A 16 point template of the heartbeat starting at the onset is also determined. Beats are then classified in a two step process; first, by template comparison with a previously determined dominant template, and second, by a finite state machine process based on the results of the template comparison and relative timing of the beat. As a result of the two step classification beats are classified as belonging to a plurality of beat types including both single and sequence beat types. A class record for each beat type is created and stored, any portion of which is accessible for display upon demand.

16 Claims, 15 Drawing Figures

| CLASS IDENTIFIER |
| --- |
| NO OF EPISODES IN CLASS |
| TIME OF LAST OCCURRENCE |
| COUNT OVER LAST 1HR; 2H; 8HR; 24HR/60 INTERVALS |
| TEMPLATE RECORD |
| WAVEFORM RECORD |
| 8 BEAT AVG'D. R R INTERVAL |
| 8 BEAT AVG'D. WIDTH |
| 8 BEAT AVG'D. PEAK TO PEAK |

| State \ Token | Dp | D | Np | Nr | NI | Ap | Ar | AI |
|---|---|---|---|---|---|---|---|---|
| entry | LD-BEAT st-paws | LD-BEAT st-paws | LD-BEAT acc-np | --- conf-nrnl | --- conf-nrnl | --- Ap-1st | --- conf-pabn | --- conf-pabn |
| conf-nrnl | DO-DOM entry | | | | | | | |
| conf-pabn | DO-PACED/ ABN/AVP entry | | | | | | | |
| AP-1st | DO-ABN entry | ↑ | UPDATE-BQ cpl- | DO-ABN entry | ↑ | UPDATE-BQ cpl- | DO-ABN entry | ↑ |
| CPL- | DO-CPL entry | ↑ | UPDATE-BQ TPL- | DO-CPL entry | ↑ | UPDATE-BQ TPL- | DO-CPL entry | ↑ |
| TPL- | DO-TPL entry | ↑ | DO-RUN ACC-RUN | DO-TPL entry | ↑ | DO-RUN ACC-RUN | DO-TPL entry | ↑ |
| acc-run | DO-RUN entry | ↑ | INC-RUN | DO-RUN entry | ↑ | INC-RUN | INC-RUN | DO-RUN entry |
| acc-np | DL-BEAT entry | ↑ | IN-BEAT | DL-BEAT entry | --- | --- | --- | ↑ |
| acc-dp | IN-BEAT --- | --- entry | | | | | | |
| st-paws | IN-BEAT/ DO-DOM acc-dp/ entry | DO-DOM entry | | | | | | |

FIG. 14

METHOD AND APPARATUS FOR ECG RHYTHM ANALYSIS

BACKGROUND OF THE INVENTION

The present invention relates to electrocardiography (ECG) and more particularly to rhythm analysis of electrocardiographic signals.

Various devices are known for monitoring heart functions and analyzing signals to assess and aid in diagnosis of a patient's heart condition. Many of these devices make use of the QRS complex region of the ECG waveform to detect heartbeats and to characterize the beat as falling within one of several morphological categories for a particular patient, such as normal or a plurality of abnormal categories. Often these devices are equipped with an alarm which is triggered when the device has detected certain predetermined electrocardiographic patterns which correspond to certain dangerous heart conditions such as ventricular fibrillation, for example. Examples of above described prior art devices are found in U.S. Pat. Nos. 3,759,248; 4,023,564; 4,336,810; and 4,360,030.

However, despite the many benefits of the prior art devices, the state of the art for heartbeat rhythm analysis is not without its problems. The timing, shape, and other characteristics of the QRS complex vary greatly among patients and it is highly desirable that ECG monitoring and analysis devices be designed to detect, characterize, store and display a wide variety of ECG signals relating to various types of heart conditions and to provide trend data associated with such conditions. Further, it is common in the state of the art today to find device false alarm rates in the range of 30% to 50% due to effects of noise. Such noise includes 60 cycle superimposition and other electromagnetic interference from electronic equipment found in hospitals today. Also, false alarms by state of the art devices are triggered by responding to high frequency muscle noise occurring concurrent with heart contractions. Also, abrupt base line shifts brought on by patient movement and respiration cause false alarms.

SUMMARY OF THE INVENTION

An object of the present invention is to provide an improved method and apparatus for electrocardiographic signal analysis.

A further object of the present invention is to provide the above mentioned method and apparatus which shows improved performance in the presence of noise.

Another object of the present invention is to provide an improved method and apparatus for electrocardiographic signal analysis including accurate and wide ranging characterization of ECG signals.

Still a further object of the present invention is to provide the above mentioned method and apparatus of the preceding paragraph which also provides an improved capability to store and display characterization and trend data associated with the analysis of ECG signals.

In the present invention ECG signals are analog filtered and then converted to a digital, representation. The sample values are then digitally filtered and then a preselected portion of the continuous digital data stream is stored at any one time in a sample buffer. A beat detection programming routine operates on data stored in the buffer to detect heartbeats and the timing of heartbeats by: detecting candidate heartbeats; identifying those candidates which are due to noise and discarding same; and providing various intra and inter beat information once actual QRS complexes are identified.

Beat information including timing and beat type, such as paced, noisy or abnormal, is provided to a beat classification programming routine which further characterizes the beat as one of a plurality of classifications most helpful to an attending physician by: identifying the heart beat as falling within one of several categories including dominant, noisy and abnormal; further processing beat information with subsequent beat information to characterize certain preselected beat sequences of importance and interest; and providing the classification information to a data base programming routine.

The data base programming routine creates class and trend records in response to beat and classification information received from the beat detection and beat classification programming routines, respectively. Each class record contains information about the classification type, number of beats classified in the class record, and a representative waveform of the class record beat. These are available to the physician for display through a user interface switch. For any class record, the physician can call up the class record information including the sample waveform for display. A separate trend record tallies how many times during a prior interval of time a beat occurred for each class. This information is also available for display.

During start up of the equipment, a special learn mode is employed by the previously described programming routines to determine certain initial state conditions required to initialize the system.

DETAILED DESCRIPTION OF THE INVENTION

Figure 1:
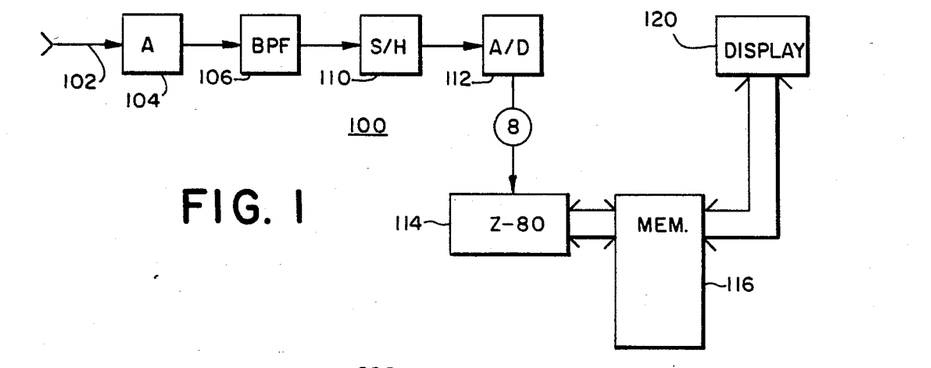
FIG. 1 is a high level block diagram of the preferred embodiment of the present invention.

FIG. 1 is a block diagram of the overall ECG rhythm analyzer of the present invention designated generally 100.

The signals from a single standard ECG lead 102 attached to a patient in conventional manner are amplified in amplifier 104 and passed through a bandpass filter 106 (0.5 to 80 Hz). The filtering is provided to reduce base line shift noise (below 0.5 Hz) and to prevent aliasing from frequencies above 80 Hz.

The signals are sampled 128 times per second by sample and hold circuit 110 and then converted to eight bit digital signals by A/D converter 112. The digital signals from A/D converter circuitry 112 are transmitted in parallel to the Z-80 microprocessor 114 where they are low pass filtered below 26 Hz by a digital filter implemented in software in conventional fashion. The filtered signals are then provided to a first circular buffer within the RAM portion of memory 116 capable of storing 16 seconds of continuous digital ECG samples (approximately 2048 8 bit words or bytes). At a sampling rate of 128 samples per minute, a new sample word is provided to the first circular buffer approximately every 8 milliseconds.

The low pass filtered digital data are also high pass filtered above 1.3 Hz by a digital filter implemented in software in conventional fashion. This filtered data is decremented by one half and provided to a second circular buffer within the RAM portion of memory 116 capable of storing 64 8 bit words of ECG data covering the same 16 seconds of data stored in the first circular buffer.

Figure 2:
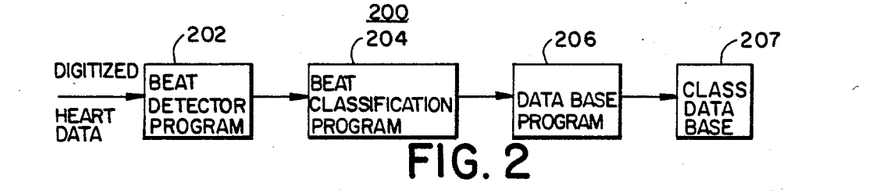
FIG. 2 is a high level block diagram of the digital processing portion of the present invention.

FIG. 2 is a high level block diagram of the digital processing program portion of the ECG rythm analyzer designated generally 200. The first and second circular buffers contain 16 seconds of continuous digital data. The beat detector portion 202 of the program 200 by continually accessing portions of the data in the circular buffers detects QRS complexes in the presence of noise, determines the peak of the R wave, the location of the QRS onset and offset, the QRS complex peak to peak, and inter beat characteristics, including the R-R interval, the average R-R interval; and the relative timing of the beats, e.g. early, normal, late. The beat detector also provides a 16 word sample of the complex starting at the onset and specifies whether the beat is noisy or non-noisy.

This information is gathered together by the beat detector 202 and forwarded as a message record to the beat classification program 204.

The beat classification program 204 comprises two steps. First, the 16 point template taken from the message record for each beat is matched against the template which is formed during a learn mode of operation of the analyzer which will be described in more detail hereinafter. If no match is found, then the incoming template is cross-correlated with the dominant template. If there is still no match, then the incoming template is classified as abnormal. During the second stage of classification, a sequence of beats is examined to determine whether or not the sequence is of particular interest and should be treated as a separate class, for example, as a couplet, triplet, a run or tachycardia. The beat classification portion 204 is capable of classifying eight different classes of abnormal, eight classes of couplets, eight classes of triplets, 16 classes of runs, one class of missed beats, one class of tachycardia, one class of ventricular fibrillation, one paced class and one AV-paced class.

Figure 3:
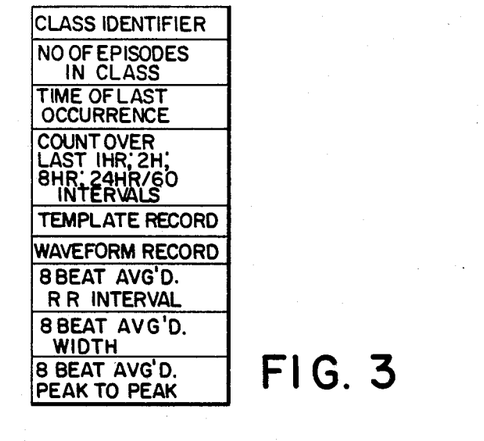
FIG. 3 is a block diagram showing the structure of a class record created by the digital processing portion of FIG. 2.

The classification of each beat as determined by the beat classification program 204 is forwarded then to the data base program 206 where a data base 207 comprising a plurality of class records is formed. Each class record 300 comprises a class identifier, the number of episodes classified in the class, the time of last occurrence of a beat classified in the class, a trend record, a template, a three second waveform of the first beat to enter the class, and message record information relating to the R-R interval, QRS complex width and peak to peak. In the case of a class record covering a sequence of beats, only the information for the first beat in the sequence is kept except that a three second waveform showing a sample of the sequence is kept.

The trend record covers an extended period of time and shows how often within periodic intervals within the extended period beats or beat sequences of each class occurred. The class records are stored in memory 116 and are transferred to display 120 by a direct memory access (DMA) upon command by the attending physician. Thus, an extensive and comprehensive description of a wide variety of recently occurring morphological conditions of a patient's heart with reduced incidence of false alarm is created for study by an attending physician.

DESCRIPTION OF BEAT DETECTION

Figure 4:
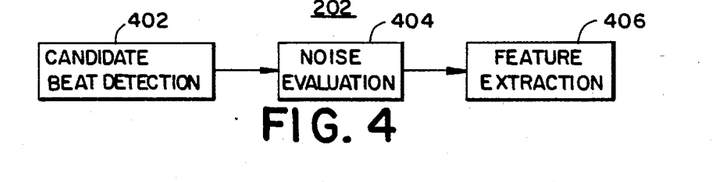
FIG. 4 is a block diagram of a beat detection program portion of the digital processing portion of FIG. 2.

Referring now to FIG. 4, the beat detection program 204 comprises a candidate beat detection portion 402, a noise evaluation portion 404, and a feature extraction portion 406. The candidate beat detection mode 402 looks for the QRS complex of one of the several ECG signals presumably present in the 16 second sample stored in the first circular buffer. The first circular buffer is used since it is desirable during the beat detection portion to operate with the data best representative of the signal coming directly from the patient. In order to find candidates, it is necessary to know an approximate value for the average R-R interval (average time between successive beats) and upper and lower tolerance values relating to the maximum amplitude differences occurring between successive signal samples in the QRS complex region. These values are determined initially during a learn mode when the equipment is first turned on. The learn mode will be described in more detail hereinafter in connection with FIG. 12.

1. Candidate Beat Detection

Figure 5:
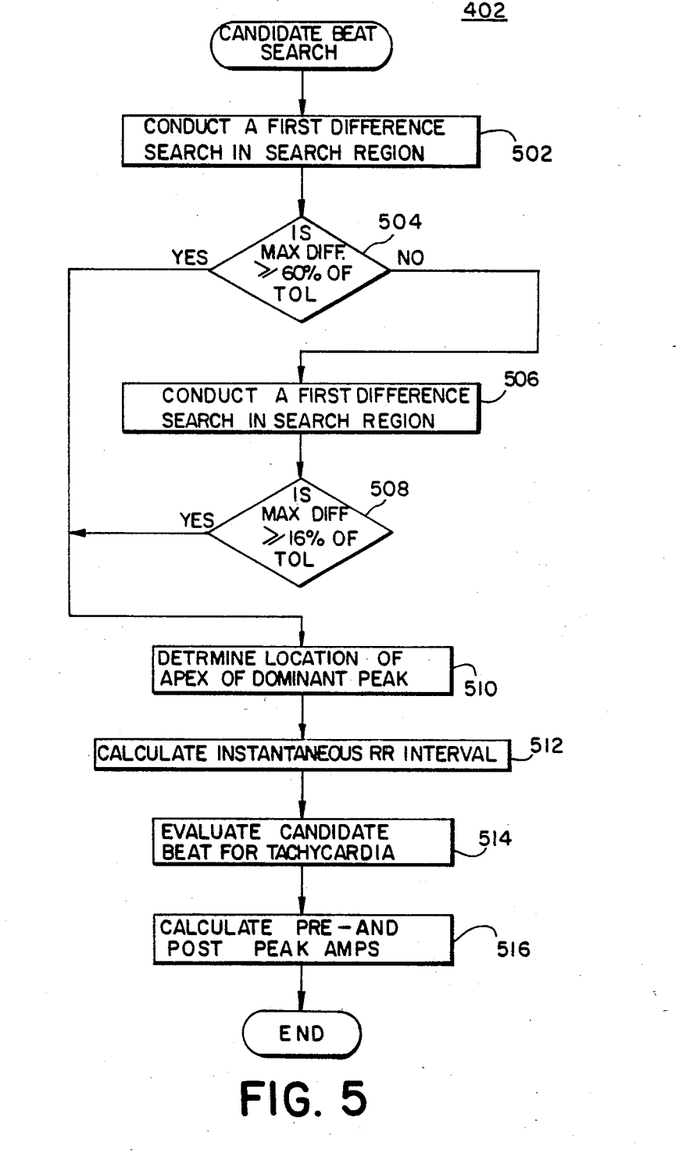
FIG. 5 is a more detailed block diagram of a first portion of FIG. 4.

Referring now to FIG. 5, a more detailed description of the candidate beat detection portion 402 is provided. A first difference search is conducted in a search region to locate the beginning of a high frequency region which in the noise free heart cycle is in the region of the QRS complex 502. The search region is defined as the time interval equal to 1.2 times the average R-R interval. The average R-R interval is described in more detail hereinafter. During initial start-up an R-R interval is provided by the program operating in the learn mode. Presumably, the QRS complex will be located in the search region. A first difference search is equivalent to determining the absolute value of the difference in amplitude between two adjacent sample points at a given location in the search interval. The location is continually incremented throughout the search interval until a first difference value is found which is equal to or greater than an upper tolerance value set equal to 60% of the absolute maximum first difference value set during the learn mode 504. If no first difference value is found in the search interval to exceed the upper tolerance value, then the search of the interval is repeated 506 to find a first difference value greater than or equal to 16% of the absolute maximum first difference value in the search interval 508.

Once a candidate peak has been located, it is desirable to locate the apex of the dominant peak in the QRS complex using a weighted convolution equation modeled for 100 millisecond peak detection 510. For all points falling within an interval bewteen the locations of the first difference between samples exceeding the upper or lower tolerance and the location occurring 19 samples later (150 milliseconds) the following amplitude is determined:

Convolution Ouput=Absolute Value of [(2 * Sphb(index))−Sphb (index−10)−Sphb (index+10)]

where Sphb (index) is the amplitude of the sample at a particular point in the 150 millisecond interval, Sphb (index−10) is the amplitude of the sample occurring 10 samples earlier and Sphb (index+10), the amplitude 10 samples later. The sample location where the Convolution Output is an absolute maximum is the apex of the dominant peak of the QRS complex, called the peak point.

Once the peak point is fixed, the instantaneous R-R interval is calculated by calculating the time interval between the current peak point and the last validated beat's peak point 512. From the instantaneous R-R interval, a determination is made if a tachycardia environment exists 514. For example, the present and last instantaneous R-R intervals are both examined to determine if both are less than predetermined time intervals. If they are both less than a particular predetermined time interval, then a tachycardia heart rate of a particular value is assigned corresponding to the particular predetermined time interval identified. In particular, for current and previous instantaneous R-R intervals, <400 millisec: 150 heart beats/min.;
<300 millisec: 200 heart beats/min.;
<250 millisec: 240 heart beats/min.

Following a determination of the instantaneous R-R interval and evaluation of tachycardia, the pre-peak and post-peak interval amplitudes are calculated for later use 516. The amplitude of a sample occurring eight samples before the peak (approximately 60 milliseconds) is subtracted from the peak amplitude to find the pre-peak interval amplitude, and the amplitude of a sample occurring eight samples after the peak is subtracted from the peak to determine the post-peak amplitude. This completes the candidate beat detection portion of the beat detection program routine.

2. Noise Evaluation

Figure 6A:
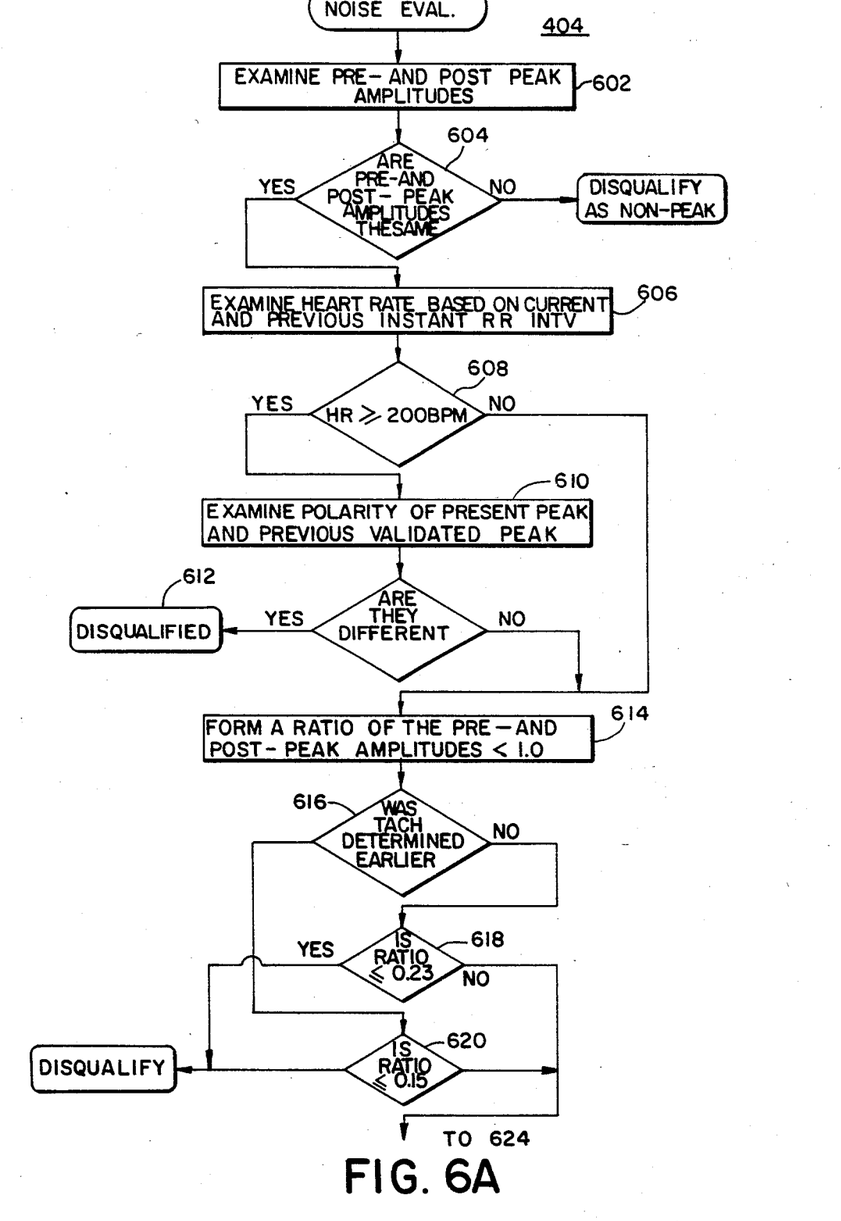
FIGS. 6A and 6B are a more detailed block diagram of a second portion of FIG. 4.
Figure 6B:
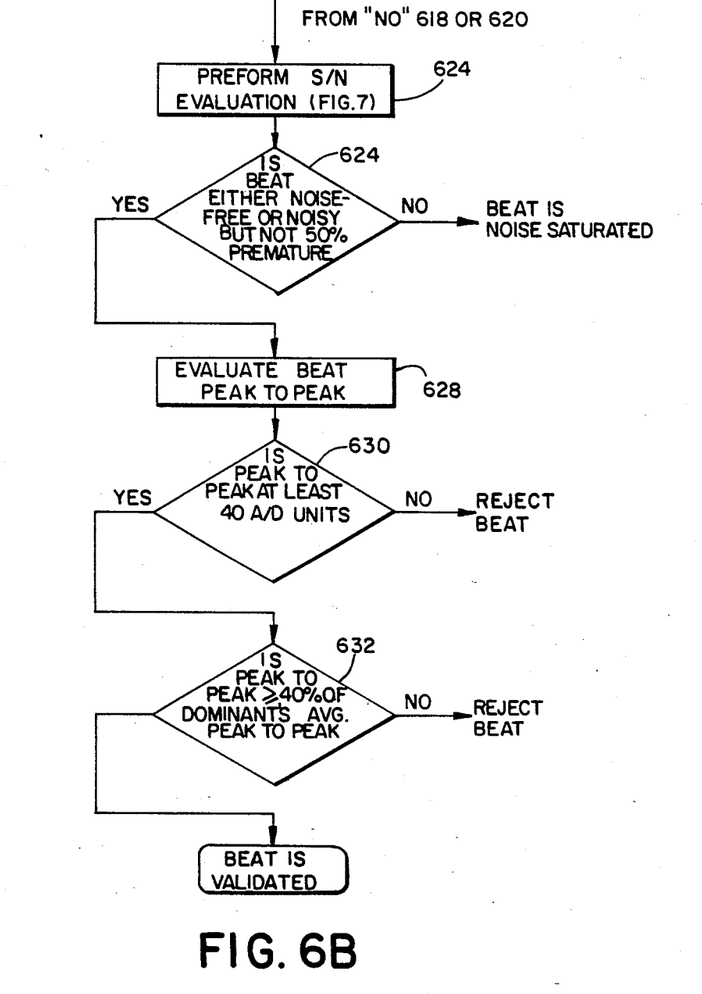

Once a peak has been located it must be validated as a QRS complex. Validation includes noise detection and noise level assessment which are used to accept or reject and or label the beat as noisy. Referring now to FIGS. 6A and 6B a series of noise evaluations are made on the candidate peak. First, the signs, either positive or negative, of the pre and post-peak interval amplitudes calculated earlier are examined 602 and if the signs are different, then the candidate is disqualified as a non-peak 604. With a true peak, the signs of the amplitudes will be the same. However, noise like base line shifts can result in a detected peak wherein the pre and post amplitude interval signs are different.

Next, if the present and previous instantaneous R-R intervals as determined by the apex of the peak each correspond to a heart rate greater than or equal to 200 BPM, then the polarity of the present peak and previous validated peaks are examined. See 606, 608 and 610. If the polarities are different, then the candidate is disqualified for an invalid peak polarity 612 since, during a tachycardia event, the candidate peak detector may be detecting the adjacent minimum and maximum points of a single beat occurring in a series of rapidly occurring beats.

A third check performed on the candidate is to evaluate the duration of the peak. This is done by forming a ratio between the pre and post-peak interval amplitudes 614. The numerator and denominator positions are always assigned to insure that the ratio is less than one. If the ratio is less than or equal to 0.23 then the candidate peak is disqualified as noise unless earlier a tachycardia condition was determined from the instantaneous R-R interval as described above, then the ratio must exceed or equal 0.15 or the candidate is disqualified. See 616, 618 and 620.

Following evaluation of the duration of the peak, the candidate peak's signal to noise (S/N) level within a defined interval about the apex of the dominant peak is assessed 624. As a result of the S/N evaluation, the candidate will be classified as:

(1) noise free;
(2) acceptable
  noise spike
  contamination
  - noisy; or
(3) unacceptable
  noise spike
  contamination
  - OVR 626.

Figure 7:
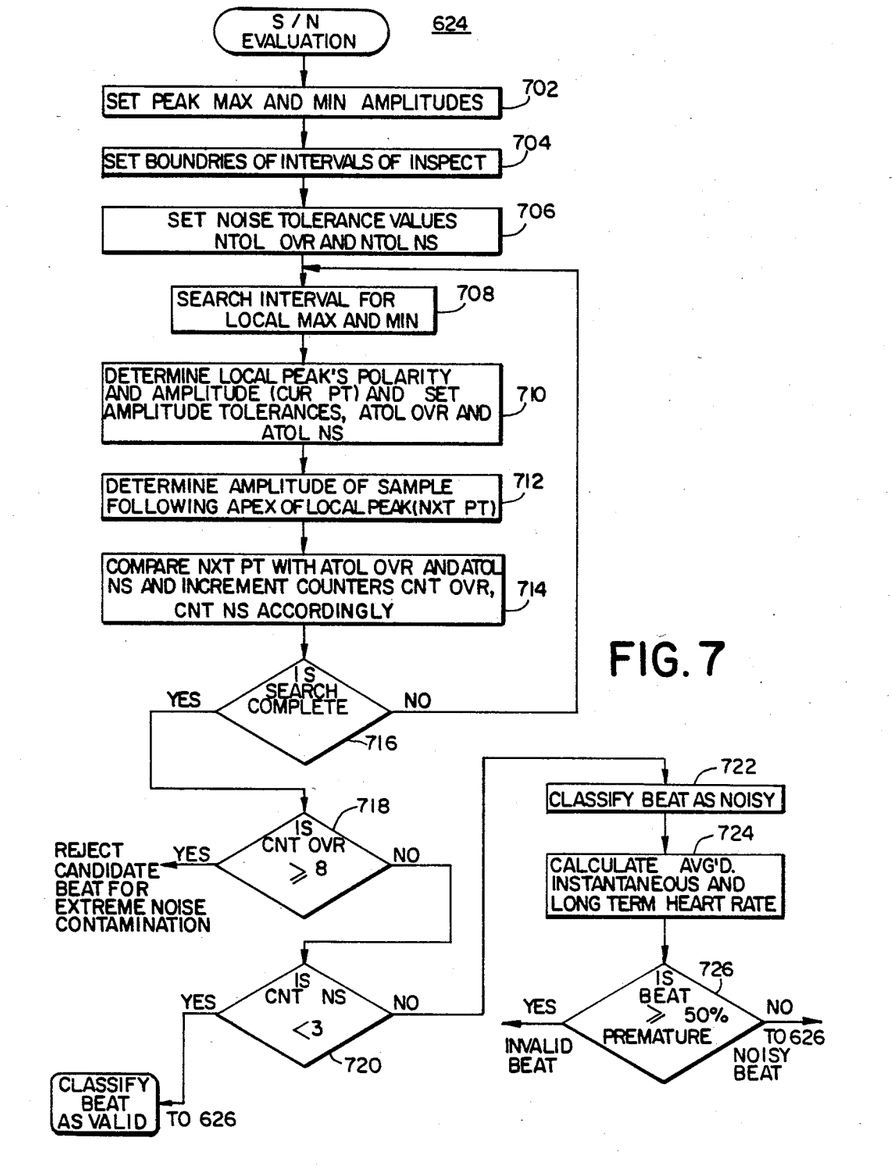
FIG. 7 is a more detailed block diagram of the signal to noise evaluation portion of the FIGS. 6A and 6B.

Referring now to FIG. 7, a more detailed description of S/N evaluation 624 is provided. The first step in S/N evaluation 624 is to initialize or set several parameters. The apex of the candidate peak, as determined by the convolution step earlier, is set as the maximum or minimum amplitude depending on the polarity of the peak 702. The amplitude of the sample occurring 50 milliseconds before the apex is set as the other extreme, i.e. as minimum or maximum, respectively as the case may be.

Figure 8:
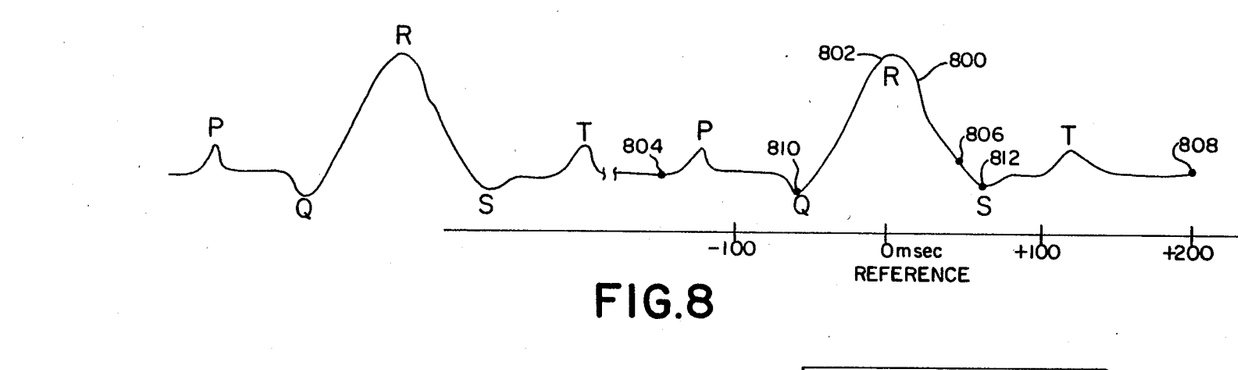
FIG. 8 is a graph of time vs. amplitude representative of an ECG signal showing the QRS complex.

Next, referring for the moment also to FIG. 8, the boundaries of the intervals of inspection which include the peak 800 are determined 704 as a function of location of the apex 802 of the candidate peak. The left boundary 804 occurs 150 milliseconds before the apex (19 samples); the left ST boundary 806 occurs 50 milliseconds after the apex (six samples); the right boundary 808 occurs 200 milliseconds after the apex (26 samples); the first peak to peak window 810, 60 milliseconds before the apex (8); and the second peak to peak window 812, 60 milliseconds after the apex (8).

Finally as part of initialization, a noise tolerance overflow value (NTOL OVR) is assigned as 15% of the peak output value as determined by the convolution calculation performed earlier. A noise tolerance noisy value (NTOL NS) is defined as ten (10) A/D units 706.

Starting at the left boundary 804, a search is begun for a local maximum or minimum. This is done by searching for a change in slope (sign) between two successive first differences. When a local maximum or minimum is located, a determination of its polarity is made depending on the sign of the previous first difference. (For example, if the first difference just before the peak is positive then the local peak is a maximum otherwise it is a minimum.) If the local peak is a maximum, tolerance values are assigned as follows:

ATOL OVR=CUR PT+NTOL OVR

ATOL NS=CUR PT+NTOL NS where CUR PT is the peak amplitude of the local maximum. If the local peak is a minimum, then

ATOL OVR=CUR PT−NTOL OVR

ATOL NS=CUR PT−NTOL NS.

See 710. When the local peak is a maximum then the larger of ATOL OVR or ATOL NS is called MAX ATOL. When the local peak is a minimum then the smaller of ATOL OVR or ATOL NS is called MAX ATOL.

Once the amplitude tolerance value parameters are set up as above for the candidate local maximum or minimum, the candidate local peak is evaluated to determine its effect on the noise level. In preparation for this, the amplitude of the sample point following the apex of the local peak is determined (NXT PT) and the slope between CUR PT and NXT PT is determined to verify that the local peak is indeed a maximum (minimum) 712.

Next NTX PT is compared with ATOL OVR and ATOL NS. When NTX PT is greater (lesser) than MAX ATOL, then counters CNT OVR and CNT NS are incremented unless the MAX ATOL=ATOL OVR. If MAX ATOL=ATOL OVR then CNT OVR is incremented and CNT NS is incremented only if the local peak being evaluated falls within the ST region, i.e., after point 812.

If NTX PT is not greater (lesser) than or equal to MAX ATOL and MAX ATOL is not equal to ATOL OVR, then the CNT OVR is incremented if NTX PT is greater (lesser) than or equal to ATOL OVR. The CNT NS is only incremented if NXT PT is greater (lesser) than or equal to ATOL NS and the local peak falls after point 812, i.e., in the ST region. See 714.

After each local peak has been evaluated for its contribution to the noise in the above manner, the next candidate noise peak in the interval containing the candidate beat is identified and evaluated and so on until the entire interval has been searched 716.

Figure 9:
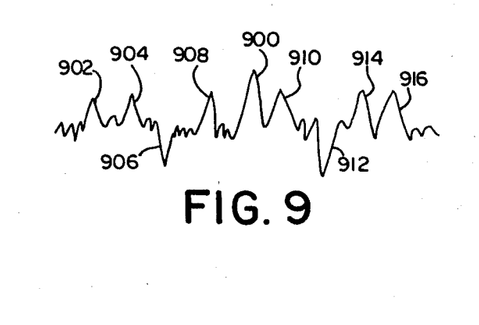
FIG. 9 depicts a heartbeat in the presence of high level noise.

Then if the count in CNT OVR exceeds a predetermined amount, e.g., eight 718, then the candidate beat is rejected for extreme noise contamination. FIG. 9 shows an example of a possible beat 900 adjoined on either side by an interval containing large noise spikes even numbers 902–916. In this instance, the central peak 900 may represent a beat but where there are at least eight other peaks, plus or minus, falling within ±150 milliseconds of the central peak and having an amplitude greater than ATOL OVR, the beat is rejected.

If the count in CNT OVR does not equal or exceed 8 and the count CNT NS is less than a predetermined number, e.g. 3, 720 then the candidate QRS complex is considered valid from a signal to noise perspective. However, if the count CNT NS is equal to or greater than 3 then at the very least the candidate beat is considered to be noisy 722. CNT NS represents the number of peaks that occurred during the ST region of the beat which had an amplitude exceeding a predetermined level. Remember a count was added to CNT NS when the amplitude of the sample following the local peak NTX PT, occurring in the ST region (after point 812) exceeded the amplitude of the local peak plus 10 additional A/D values for a maximum local peak or was less then the amplitude of the local peak minus 10 additional A/D values for a minumum local peak. Since there should be relatively very little high frequency activity present in this region three peaks (plus or minus) of sufficient magnitude classifies the candidate QRS complex as noisy.

If a beat is classified as noisy and the number of previous R-R intervals which have been averaged to obtain a heart rate calculation (to be described in more detail hereinafter) is greater than zero then:

(1) a heart rate average, HRAVRR is formed, HRAVRR=constant/RR inverval averaged over the 32 most recent nonpremature beats;

(2) an instantaneous heart rate average, HRINSTRR is formed, HRINSTRR=constant/No. of samples between present local peak apex and apex of last validated peak; and (3) a 50 percent factor is formed, PCNT 50=(½)(HRAVRR). See 724.

If the instantaneous heart rate, HRINSTRR, is less than HRAVRR plus PCNT 50 then the noisy beat is not premature, otherwise not only is the beat noisy but also 50 percent premature and therefore held to be invalid 726. The constant chosen above is 7680 which is the number of 8 KHz samples present in a single minute. Thus the calculations above for HRAVRR and HRINSTRR result in a heart rate measured in beats per minute, BPM.

Referring back to FIG. 6B, when the S/N evaluation is over a final noise quality check is performed on the peak to peak. The peak to peak of the QRS complex is determined by taking the absolute value of the difference between the maximum and minimum amplitudes of the candidate beat set at the beginning of the S/N evaluation 628. The peak to peak of the candidate beat must be a minimum of 40 A/D values 630 and at least 40% of the dominant's average peak to peak 632.

3. Feature Extraction

Figure 10:
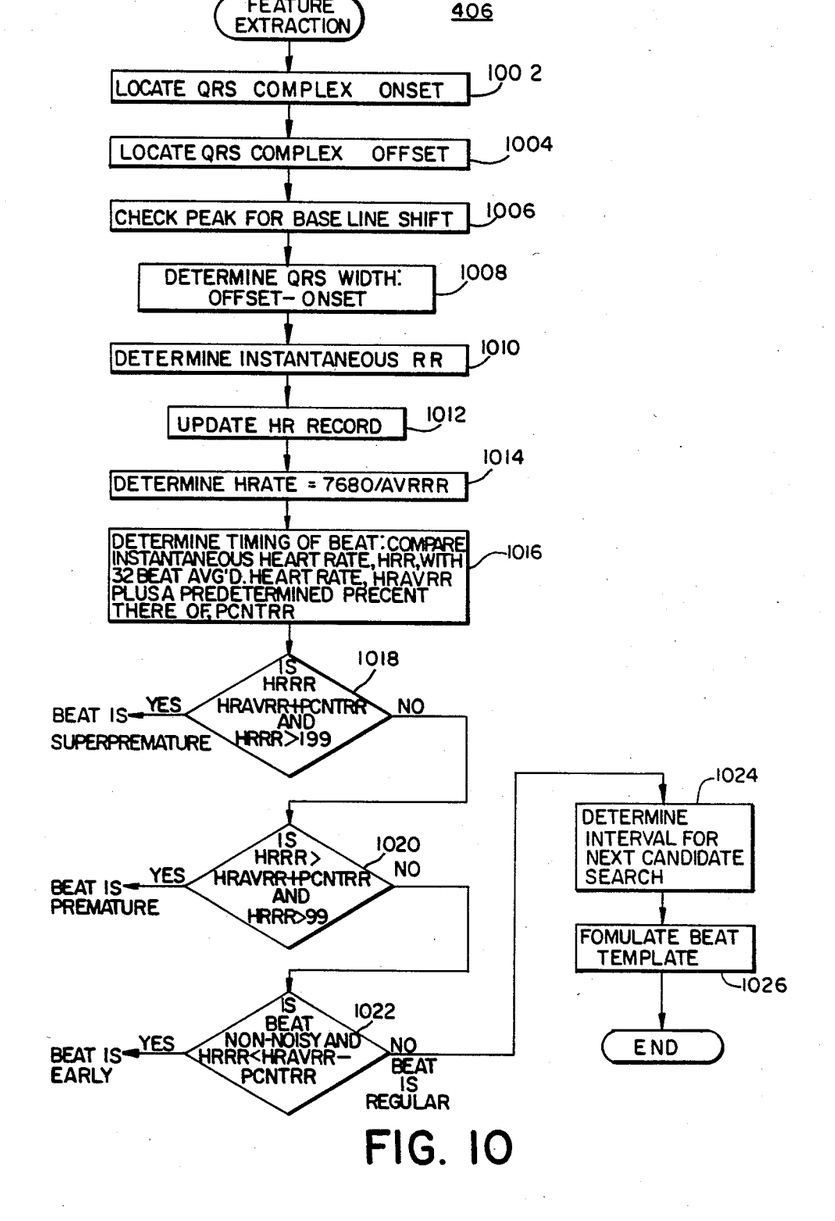
FIG. 10 is a more detailed block diagram of a third portion of FIG. 4.

Referring now to FIG. 10, following beat detection 402 and noise evaluation 404 as described so far above, the features of the QRS complex are extracted 406. These features include QRS onset and offset; QRS width; heart rate (HRATE); and the timing of the beat as premature superpremature, regular or late.

To determine the onset a backward difference search is conducted beginning in the region of the apex of the dominant peak to locate the beginning of a low frequency region. More specifically a search is conducted in the region starting 30 msec before the apex and proceeding backward to a point 150 msec before the peak 1002. When three consecutive first difference amplitudes are found which are less then a predetermined value, then the onset is assigned to the location of the first sample involved in the three consecutive first differences determination. The predetermined value in the preferred embodiment is the lower tolerance value (16% of absolute maximum first difference found in the original search interval) used earlier to find a candidate peak. If no onset is found then the search is repeated in the same region but the predetermined value is changed to an intermediate tolerance value equal to 30% of the absolute maximum first difference found in a search interval during the learn mode. If an onset is still not found the onset is set at 30 msec before the apex of the QRS complex.

Once the QRS onset is found (onset is considered the QRS fiducial point), it is necessary to determine the end of the QRS complex, called offset 1004. This is accomplished in a manner similar to determination of the onset, namely a forward difference search beginning in the region of the apex of the dominant peak is conducted to locate the beginning of a low frequency region. More specifically the region between 30 msec and 150 msec after the apex is searched until six consecutive first differences are found whose amplitudes are less then the lower (16%) tolerance value. The offset point is the location of the first sample involved in the six consecutive first differences determination. If no offset is found then the search is repeated using the upper (60%) tolerance value. If no offset is found it is set at 30 msec after the peak.

If the beat had been identified as noisy, i.e., during S/N evaluation the CNT NS is greater than or equal to three but less than eight, but the beat was not part of a tachycardia sequence greater than 200 BPM, then the onset and offset points are assigned at ±30 msec from the peak, respectively. If the noisy beat is part of a 200 BPM tachycardia then onset is set at −30 msec and offset is set at the dominant beat's peak.

If the onset value of the current beat is greater than or equal to 50 msec and the beat has not been assessed as noisy, then the beat is checked again for a baseline shift 1006. This involves making a preliminary determination of the timing of the beat and a comparison of the average amplitude in the pre peak low frequency zone with a median amplitude value preset during initialization in the learn mode.

With respect to the preliminary timing step mentioned above, the instantaneous heart rate, HRRR, given by

HRRR=7680/RR INTV, where RR INTV is the instantaneous R-R interval based on the onsets of the present and prior validated beats, is determined. If HRRR<HRAVRR (defined earlier) plus 18% of HRAVRR, then the timing of the beat is OK, i.e. it is not premature. Following this determination, if the beat is not premature, then the amplitudes of the samples from the second circular buffer for the 50 msec prior to the apex of the beat are averaged. If the absolute value of the difference between the median value 128 and the average is greater than 20 then the beat is considered noisy and a baseline shift is said to have occurred. 128 is chosen since during the learn mode the low frequency intervals and inter beat intervals of the ECG signals are calibrated to fall at an A/D output value of 128.

The remaining features to be extracted are: the QRS complex width 1008, which is determined by finding the difference between the offset point and onset point; various averaged heart rates; and a classification of the timing of the beat. In preparation for computing the heart rates and beat timing the instantaneous R-R interval (RR INTV) is determined by finding the difference between the onset of the present beat and the onset of the last validated beat 1010.

The heart rate (HRATE) then is determined from a heart rate (HR) record formed in memory 142 from the present and prior RR INTVs of validated beats 1012. The HR record contains an average RR (RR intervals averaged over the seven previous and present RR); a sum of the seven previous and present RR; the number of RR intervals averaged so far; and a circular buffer containing the 8 most recent RR's. These are identified as AVRRR, SUMRR, NUMRR and RR [Array] respectively. The heart rate then is determined by, HRATE=constant/AVRRR where the constant equals 7680. 7680 is the number of 8 millisecond samples closest to one minute in duration. If 8 RR's have not yet occurred then the HRATE is determined using the sum of the number of RR's determined thus far divided by that number. See 1014.

Following a determination of the HRATE, the timing of the beat is determined by comparison with a longer term average RR interval 1016. For this calculation an average RR value is used derived from an averaged heart rate record (AVRR) similar to the HR record and containing an AVRRR averaged over the 32 most recent nonpremature RR's.

HRAVRR=7680/AVRRR (from AVRR record)

and

HRRR=7680/RR INTV

If the beat had previously been labelled as noisy then a precentage factor PCNTRR=30% HRAVRR is added to HRAVRR, otherwise, PCNTRR=18% HRAVRR is added to HRAVRR.

If HRRR>HRAVRR+PCNTRR and HRR>99
Then the beat is premature (1020)
If HRRR>HRAVRR+PCNTRR and HRR>199
Then the beat is super premature (1018).
If the beat is not noisy and
If HRRR<HRAVRR−PCNTRR
Then the beat is late (1022).

Following assesment of beat timing, the interval region for the next candidate search is determined based on the most recent instantaneous RR INTV 1024.

If RR INTV<200 msec
Then FRST PTX=OFFSET+50 msec where FRST PTX is the location of the first sample in the new search interval.
If 200 msec<RR INTV<500 msec
Then FRST PTX=OFFSET+150 msec otherwise FRST PTX=OFFSET+250 msec
If a tachycardia of 150 is indicated
Then FRST PTX=OFFSET+(0.75) RR INTV and LAST PTX=PEAK PT+CAND REG where PEAK PT is the location of the apex of the dominant peak and CAND REG=(1.2)(AVG RR INTV) where AVG RR INTV is the average of the present and previous RR INVT when the heart rate is greater than 150.

FRST PTX=OFFSET+(0.75)(AVRRR from the AVRR record) and LAST PTX=PEAK PT+(1.2)(AVRRR from the AVRR record)

As the last step of the feature extraction portion 406 of the beat detection program 204, a template record for the QRS complex is created 1026. Sixteen points are taken from the second circular buffer starting with the ONSET point and skipping every other point. This is equivalent to 64 sample spaces in the first circular buffer and comprises approximately 512 msec of the last waveform including all of the QRS complex.

Figure 11:
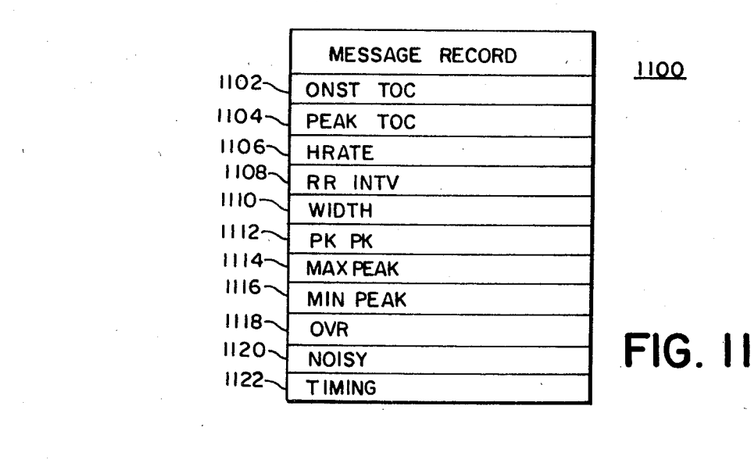
FIG. 11 is a block diagram showing the structure of a message record created by the digital processing portion of FIG. 2

All the features extracted are placed in a message record 1100. They include: the time of occurrence of beat's onset 1102; the time of occurrence of the beat's peak 1104; the heart rate averaged over the 8 most recent RR INTV's 1106; the onset to onset interval 1108; the width of the QRS complex from onset to offset 1110; the beat's peak to peak 1112; the maximum peak amplitude in the QRS region 1114; the minimum peak amplitude in the QRS region 1116; whether an overrange as occurred 1118; an indication if the beat is noisy 1120; and an indication of the beat's timing as super premature, premature or late 1122.

Figure 12:
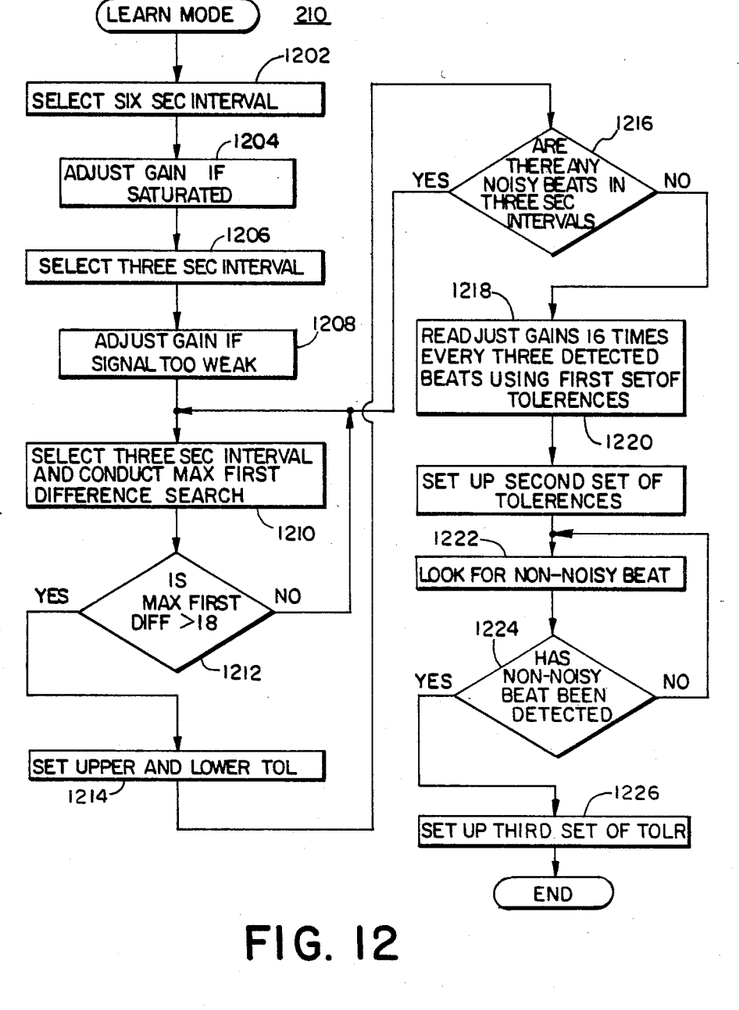
FIG. 12 is a detailed block diagram of the learn mode of the beat detection program of FIG. 4.

The parameters necessary to conduct the next candidate beat search are reset based on the last beat's parameters. The template record along with the message record are sent to the beat classification routine 204. The beat detection program 202 repeats and continues to identify candidate peaks, qualify them, extract features and form the message and template records including a preliminary classification as nominal or noisy and early, normal or late. However, before describing the beat classifier, a description of the beat detection routine's learn mode 1200 is provided.

4. Learn Mode

Referring now to FIG. 12, soon after the equipment is turned on the signal is checked for saturation and linearity. The A/D converter is capable of a range of amplitudes between 0 for the strongest signal and 255 for the weakest. It is desireable that the baseline heart signal be positioned somewhere in the middle of this dynamic range, e.g. at 128. To accomplish this a six second interval of the digitized signal in the first circular buffer 116 is identified 1202 and the signal checked therein for saturation. If it is saturated the amplification gain of the signal is automatically reduced. The signal is checked to make sure that at minimum gain the signal is not saturated, i.e. that it falls within the A/D values 16 to 239 1204. Then a three second interval is identified 1206 and the signal is checked to determine that at maximum gain the signal is not too low, i.e. at maximum gain the peaks of the ECG signal should be able to reach A/D levels of either 64 or 192 1208.

Next a three second interval is identified and a maximum first difference search is conducted 1210. If a maximum first difference greater than 18 is found an upper tolerance value equal to 60 percent of the maximum is set and a lower tolerance value equal to 18 percent is set. See 1212 and 1214. The 3 second interval is then checked using the procedure set out above to detect noisy beats. If any are found the procedure to initiate tolerances is performed again until no noisy beats are found in the 3 second interval 1216.

Using the first set of tolerances from 1214 the learn mode again adjusts the gains of the equipment in a manner as described above. This is done every three beats for 16 adjustments 1218 times. Then a second set of tolerances is obtained exactly as before checking to make sure there are no noisy beats 1220. Then using the new tolerances the beat detection program 202 is exercised again 1222 until a new non-noisy beat is found 1224. A third set of tolerances are determined as before 1226 and the learn mode is over. The beat detection program 204 operates as described earlier using the last set of tolerances.

BEAT CLASSIFICATION

Figure 13:
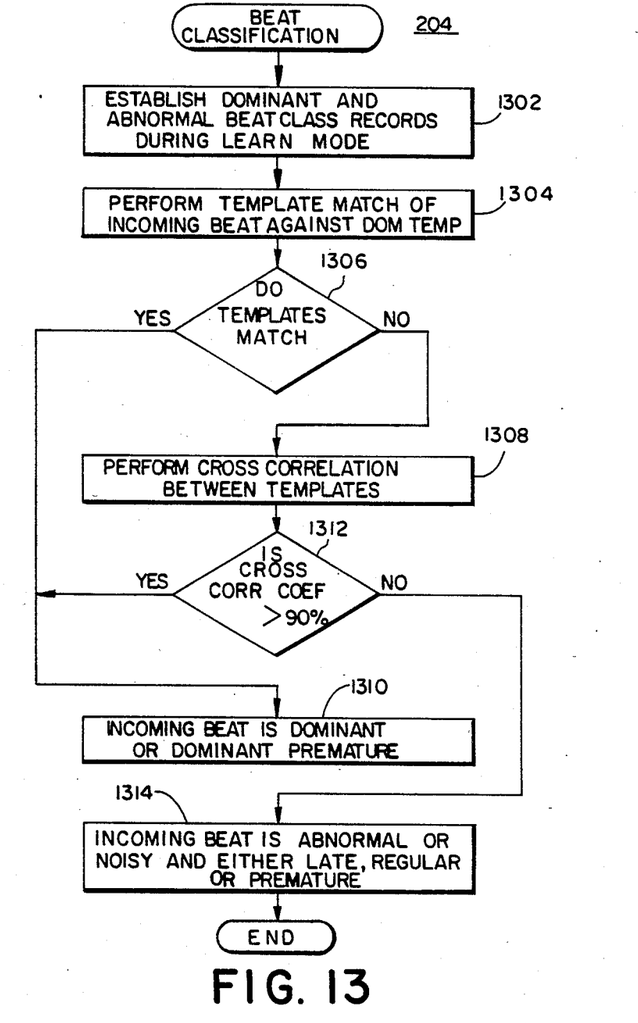
FIG. 13 is a block diagram of a first portion of a beat classification program portion of FIG. 2.

Referring now to FIG. 13, the beat classification program 204 is described. During the learn mode detected beat message and template records are provided to the beat classification program 204 where they are compared with one another in a manner to be described below and stored as separate beat classes if they are unalike. When beats are found to be the same, the class record for that beat is updated to show how many beats were found that fit the class. When the number in any one class reaches a predetermined number, e.g. 8, that class is called the dominant. See 1302.

During the normal run mode each incoming beat to the beat classification program will have been catergorized by its timing (early, regular, late) and perceived typed (paced, noisy, or nominal). Paced is a category not automatically detected by the beat detection program 202. Instead when a pace maker provides stimulus for a beat it sends a signal to the beat detection program 202 that a paced beat is present.

During the first stage of classification the template of the incoming beat if nominal or noisy is compared with the stored template of the dominant using a template matching subroutine 1304. If a match is found 1306 the beat is classified as dominant premature, Dp, or dominant, D, depending on the timing information received from the message record 1310. Dominant late and dominant regular are classified as dominant.

The template matching subroutine is as follows: each template comprises 16 points, the first of which is the onset point of the ECG complex. The template matching routine compares each point of the template with each point of the other template being compared. The 16 points of each template can be thought of as spanning two intervals, for example, interval No. 1 from onset to offset and interval No. 2 from offset to the end of the 16 points. The absolute difference is calculated between corresponding points of the templates being compared. Tolerance 1, Tol1, and Tolerance 2, Tol2, are the values of the differences allowed in the two intervals, respectively. If an absolute difference exceeds an associated Tol a violation is counted. Two templates are considered to be of the same morphology if the number of violations of the absolute difference does not exceed a predetermined count (UPCNT).

The values of Tol1, Tol2, and UPCNT vary based on the rhythm regularity, the quality of the analyzed signal and the state of the analysis. For example,

|        | Tol1 | Tol2 | UPCNT |
|--------|------|------|-------|
| Learn: | 25   | 20   | 4     |
| Noise: | 25   | 20   | 5     |
| AFIB:  | 25   | 17   | 4     |
| Other: | 20   | 15   | 4     |

Even if an incoming beat fails the template match, a cross correlation is performed between the templates 1308. If the cross correlation coefficent exceeds 90% the incoming beat is still classified as dominant 1310. Otherwise, the incoming beat is classified as abnormal late, regular or premature (Al, Ar, Ap) or if noisy, Nl, Nr, Np. See 1312 and 1314.

The formula used for determining the correlation coefficient 1308 and 1312 between two samples is:

$$C = \frac{\sum\limits_{i=1}^{N}(x_i - \bar{x})(y_i - \bar{y})}{\left(\sum\limits_{i=1}^{N}(x_i - \bar{x})^2\right)^{\frac{1}{2}}(\Sigma(y_i - \bar{y})^2)^{\frac{1}{2}}}$$

where $x_i$, $y_i$ are the points of respective templates and $$\bar{x} = \Sigma x_i/N \quad \bar{y} = \Sigma y_i/N$$

are the mean values of the respective templates. Because of the low sample rate, cross correlation starts with the template peak (to avoid the higher frequency components). Unique scaling was used to handle the impaired accuracy that is caused by using integer point calculations. The correlation coefficient used during AFIB is 0.8 otherwise it is 0.9.

As a result of the first level of classification described above in connection with FIG. 13 a beat is classified as:

D→non-premature (regular or late) dominant;
Dp→premature ($\geq 20\%$) dominant;
P→single paced beat;
AVP→atrial-ventricular paced beat;
Al→abnormal (i.e. found non-dominant) late;
Ar→abnormal regular;
Ap→abnormal premature;
Nl→noisy late;
Nr→noisy regular;
Np→noisy premature.

Additionally, there are several types of "virtual" 2beats—those representing not physically generated beats but other events of significance to the classification process. Namely:

M→missed beat. No beat was detected within 1.8 nominal beat-to-beat intervals so one has been generated;
O→Overrange event;
V→In ventricular fibrillaton.

Before continuing with a description of the classification the following notation is defined:

The right arrow (→) means "is defined as";
the vertical bar (|) means "or";
the overbar - means "not";
angle brackets (< >) enclose the name of a non-terminal construct or sequence of beats of interest; and
exponent means repetition.

Figure 14:
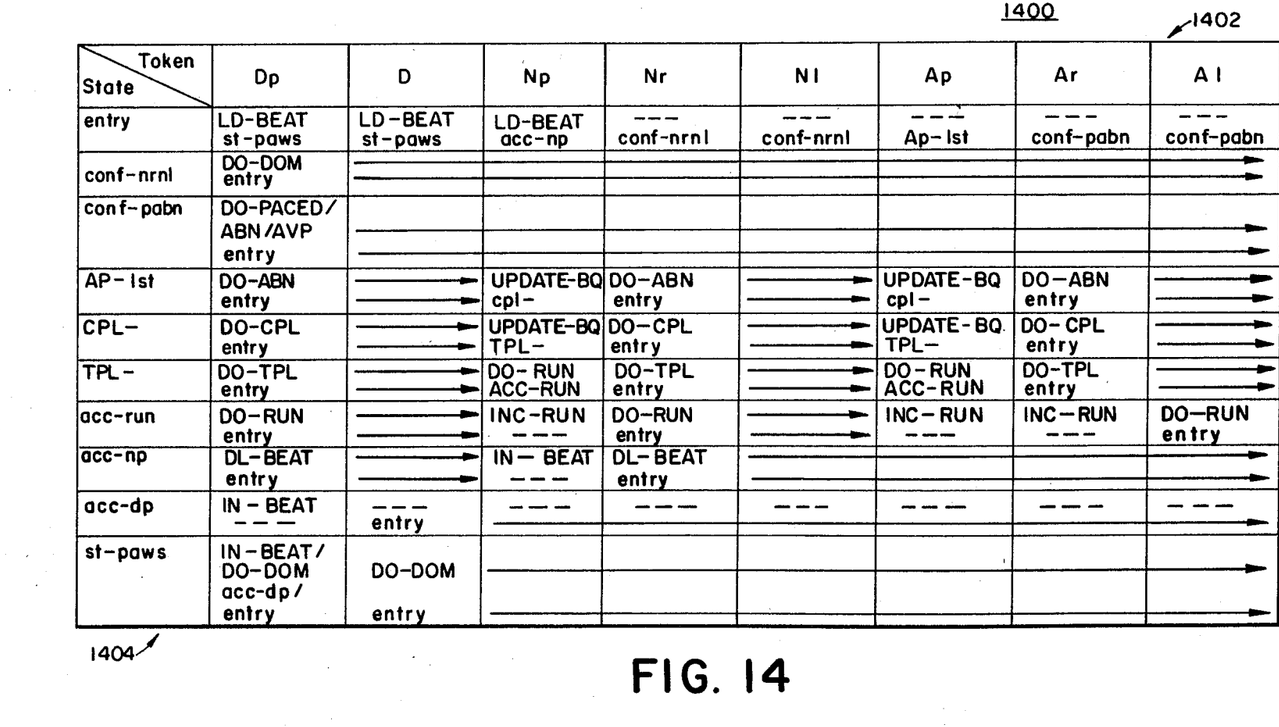
FIG. 14 is a state diagram of the beat classification program portion of FIG. 1 showing the outputs of the first portion of FIG. 1 along one axis of the state diagram.

The following grammar defines the second stage of beat classification in combination with the finite state machine of FIG. 14:

<pan>→Ap|Np
<panar>→<pan>|Ar
<paced>→P|AVP
<delm>→D|Dp|Ar|Al|Nr|Nl|<paced>|V|M
<$\overline{O}$>→<delm>|<pan>(not overrange)
<ms>→D|Dp|Al|Ar|Ap|Np|Nr|Nl|<paced>
*<domin>→D|Nr<$\overline{O}$>|Nl<$\overline{O}$>
*<paced>→P<$\overline{O}$>
*<AV-paced>→AVP<$\overline{O}$>
*<ABN>→Al<$\overline{O}$>|Ar<$\overline{O}$>|Ap<delm>
*<cpl>→Ap<pan><delm>
*<tpl>→Ap<pan>$^2$<delm>
*<run>→Ap<pan>$^n$<delm>; $n \geq 3$
*<tac>→Dp$^j$; $j \geq 5$
*<noisy-run>→Np$^k$; $k \geq 10$
*<missed>→<ddp>(M$^n$<ms>)$^k\overline{M}$; $1 \geq (k,n)$
*<vfib>→V$^k\overline{V}$ <expunged>→NrO|NlO|<paced->O|AlO|ArO|ApO|<cpl>O|<tpl>O
*Items recorded in the data base by the data base routine.

DESCRIPTION OF FINITE STATE MACHINE

FIG. 14 is a chart showing how the finite state machine designated generally 1400 operates using the nomenclature described above. The set of first level classifications of incoming beats are set out along the top horizontal axis 1402 of the chart. The possible states that the beat classification program can be in during the second stage of classification are shown along the left most vertical axis 1404. The particular state that the beat program 204 routine is in at any particular instant in time depends on the current state that the program is in and the particular first level classification of the incoming beat.

The chart then is a matrix with a location in the matrix defined by a selection from along the top horizontal axis 1402 and a selection from along the left vertical axis 1404. Each location contains two pieces of information. The first entry is the operation to be performed (the subroutine or procedure to be executed) and the second the next state that the beat classification program is to move to (the call).

Many of the morphological conditons that an attending physician is interested in cannot be diagnosed on the basis of characterization of a single beat such as dominant, abnormal or noisy. Instead, a sequence of beats is often required. For example, the occurrence of couplets, triplets and runs (2, 3 or more beats in rapid succession respectively) is of great interest as is the number of times particular beat types and sequences of beat types have occurred. The finite state machine of FIG. 14, i.e., the operation of the second level of classification of the beat classification program 204 was designed to accomplish this.

Each of the entries along the top horizontal axis has been described previously. Starting with "entry", the top state of the left vertical axis, each of the states will be briefly described. As the name implies in "entry" each new incoming beat which is not a part of a sequence of beats enters the finite state machine at state "entry". This is the initial state for any new sequences and it is the state to which the beat classification program returns when a sequence is terminated.

If either a noisy regular or noisy late pulse arrives the machine moves to the conf-nrnl state wherein a DO-DOM routine is executed. DO-DOM informs the data base routine that yet another dominant pulse has arrived. $N_r$ and $N_l$ are considered dominant for purposes of the count of the number of dominant pulses occurring.

Skipping the next state, conf-pabn, for the moment, the next state "Ap-1st" is initiated by an incoming premature abnormal pulse Ap. No operation is performed initially. If the next pulse is a <deln> (i.e. delimitor) pulse then the state "Ap-1st" is terminated, a DO-ABN action is performed and the machine returns to the "entry" state. Within DO-ABN the original Ap pulse is compared with other abnormal class records using the template matching routine to locate the class, if any, defined as headed by an Ap with the same waveform. If none exists a new abnormal class with that waveform is created. On the other hand if the next pulse is an Ap or Np then the machine enters the couplet state "CPL-" and the Ap or Np pulse is placed in a beat Q for further investigation (UPDATE-BQ).

Again looking at the chart, if the machine is in the "CPL-" state and a <deln> pulse occurs then the machine performs a DO CPL operation. This operation informs the data base routine that a couplet has occurred and sends the appropriate information to the data base routine. The machine 1400 returns to the "entry" state. However, if a third Ap or Np pulse occurs the finite state machine moves into the triplet state, "TPL-". The pulse is placed in the beat Q.

As in the case of a couplet, if the next pulse is a <deln> pulse then the machine performs DO-TPL informing the data base routine that a triplet has occurred and the machine returns to the "entry" state. However, if an Ap or Np pulse occurs next, then a run sequence of pulses is identified (DO-RUN), and the state of the machine moves to state "acc-run" for (accumulate run). In the "acc-run" state, the machine will continue to count the pulses in the run (INC-RUN) as long as Ap, Ar, or Np pulses occur. Any other pulse will terminate the run and it will be identified to the data base routine and the machine will return to "entry".

The "acc-np" state is entered when an Np pulse occurs as a lead beat (LD-BEAT), i.e. when it is the first beat occurring after the machine has returned to the "entry" state. The machine stays in this state as long as Np pulses occur. See IN-BEAT. When a <deln> pulse occurs the number of Np pulses that have occured in sequence is noted (DL-BEAT) and the machine returns to "entry".

If a D or Dp beat occures as a lead beat then the machine shifts to the st-paws state. For D beats a DO-DOM is performed and the machine returns to entry. For Dp pulses a determination is made, based on timing between successive Dp beats, whether Dp is a dominant beat or part of a premature sequence. If it is determined to be dominant, a DO-DOM is performed and the machine returns to "entry". Otherwise the machine moves to state, "acc-dp", where it remains as long as Dp pulses occur. Any other pulse will force the machine to return to entry.

Other states such as "conf-pabn", "acc-m", "acc-b" and "in-vfib" can be added. They will not be described in detail here but relate to the special condition when paced or fibrillation pulses are present or when no beats have been found (missed beats). Following the description and procedure outlined above, various other operations can be employed for characterizing various conditions using a finite state machine approach.

As described above, when the finite state machine identifies an incoming pulse as either a single pulse of particular type, such as one of the pulses listed along axis 1402, or identifies a sequences of pulses such as a couplet, a triplet, a run, etc., it so notifies the data base program 206 which updates the appropriate class record 300 in the class data base 207 if one already exists or it creates a new class record. In the preferred embodiment, there is one dominant class record, 8 different single abnormals, 8 different couplets, 8 different triplets, 16 runs, 1 missed, 1 tachycardia, 1 ventricular fibrillation, 1 paced and 1 AV-paced. The information contained in a sequence class record is that of the leading beat in the sequence.

While in the beat classification program 204 if any four consecutive beats are dominant and the RR INTV varies from the former RR INTV by more than 12.5% then a state of AFIB (actual fibrillation is described). While in this state if the RR INTV of 16 consecutive dominant beats vary from their former beats by less than 12.5% AFIB is terminated.

Based on the classification process, message record, heartrate determination and noise evaluation, all described in detail above, various alarms can be created. The simplest alarm is to send a message to the screen or turn on a light or both. Examples of alarms which are used are: class record full, a new dominant has been created, signal is too noisy, heartrate pause, existence of tachycardia, existence of couplet, triplet or run, too low heartrate, too high heartrate, ventrical fibrillation, etc.

Any or all of the data of each class record created in the data base as described above is available upon demand on a display such as CRT display 120. The class record data is transferred from memory 116 to the display by direct memory access (DMA).

What is claimed is:

1. An apparatus for automatic heartbeat rhythm analysis of ECG signals comprising:
    means for digitizing said ECG signals;
    means responsive to said digitized ECG signals for automatically detecting heartbeats including means for analyzing said detected heartbeats;
    means for assessing the relative timing of said detected heartbeats relative to prior heartbeats;
    means responsive to said analysis for classifying each of said detected heartbeats as one of a plurality of beat types, said plurality of beat types including a plurality of sequences of beat types, said classifying means further comprising:
    first stage means responsive to said timing means for automatically classifying each of said detected heartbeats as one of a first plurality of single heartbeat types; and
    state machine means responsive to said first stage classification for automatically determining when said detected heartbeats are part of one of said plurality of sequences of heartbeat types and for classifying said detected heartbeats so determined as belonging to one of said sequence type plurality, said apparatus further comprising:
    means responsive to said classifying means for automatically forming and storing class records, at least one for each of said plurality of beat types including said plurality of sequences of beat types; and
    means for displaying all or a portion of preselected ones of said class records.

2. The apparatus of claim 1 wherein said analysis by said analyzing means comprises forming a template including a plurality of digital signals representative of a portion of an associated detected heartbeat, and
    said classifying means further comprises forming a dominant heartbeat type by template comparison of detected heartbeats; and
    said first stage means further comprises means for forming a plurality of abnormal single heartbeat types by template comparison of said detected heartbeats with said dominant heartbeat template.

3. The apparatus of claim 2 wherein said means for comparing said templates comprises:
    means for determining the absolute values of the corresponding point by point differences between two of said templates;
    means for comparing the absolute values of said differences with a first predetermined number for said differences obtained over a first interval of said templates and with a second predetermined number for a second interval of said templates; and means for adding the number of times that said absolute values exceed said first and second predetermined numbers; and means for determining whether said incoming and dominant templates match in response to said number of times.

4. The apparatus of claim 1 wherein said relative timing means further comprises:
   means for automatically determining the R-R interval of said detected heartbeats;
   means for determining an instantaneous and average heartbeat in response to said R-R interval; and
   means for comparing said instantaneous heartrate with said average heartrate in a predetermined manner to determine said relative timing.

5. The apparatus of claim 1 wherein said second plurality of sequences of heartbeat types comprises:
   couplets, triplets, and runs.

6. The apparatus of claim 1 wherein said detection means further comprises:
   means for automatically detecting candidate heartbeats;
   means for evaluating the noise content of said ECG signals; said evaluating means further comprising:
   means for identifying said candidate beats as valid, noisy or invalid.

7. The apparatus of claim 6 wherein said noise evaluating means further comprises:
   means for automatically detecting local maximum and minimum peaks within a predetermined interval including said detected heartbeat;
   means for determining the number of said local peaks exceeding a first predetermined maximum or minimum signal value throughout said predetermined interval; and
   means for determining the number of said local peaks exceeding a second predetermined maximum or minimum signal value throughout a preselected portion of said predetermined interval.

8. The apparatus of claim 7 wherein said preselected portion comprises the ST portion of said ECG signal associated with said detected heartbeat.

9. The apparatus of claim 1 wherein said means for automatically analyzing detected heartbeats further comprises:
   peak detection means for automatically locating the peak of the QRS complex of said ECG signals;
   means for automatically locating the onset of said QRS complex relative to said peak locations; and
   means for automatically determining the R-R interval between the current and prior detected heartbeats in response to said onset points.

10. The apparatus of claim 9 wherein said means for automatically analyzing heartbeats further comprises;
    means for determining instantaneous and averaged heart rates in response to said R-R interval determination; and
    timing means for determining the relative timing of said heartbeat in response to said instantaneous and averaged heart rates.

11. The apparatus of claim 9 wherein said analysis means further comprises:
    means for forming a template representative of said detected heartbeat, said template beginning at said onset point.

12. The apparatus of claim 11 wherein each of said class records comprises:
    the number of detected heartbeats classified in the class;
    a trend record;
    the template of at least one of said detected heartbeats classified in said class; and
    a representative ECG waveform sample over a predetermined time interval including at least one of said detected heartbeat types of said class record.

13. A method of automatic rhythm analysis of digitized ECG signals comprising:
    detecting said heartbeats from said digitized ECG signals;
    analyzing said detected heartbeats including assessing the timing of said detected heartbeats relative to prior detected heartbeats;
    automatically classifying each of said detected heartbeats in response to said analysis as one of a plurality of heartbeat types including a plurality of sequences of heartbeat types, said classifying step including:
    identifying a dominant heartbeat type;
    comparing said detected heartbeats with said dominant heartbeat and classifying said detected heartbeats as dominant or abnormal;
    determining whether a detected heartbeat is part of one of said plurality of sequences of heartbeat types from said relative timing and said classification of said heartbeat as dominant or abnormal; and
    classifying said detected heartbeat as one of said sequence plurality when said detected heartbeat is determined to be part of one of said sequence plurality, said method further comprising:
    automatically forming and storing class records for each of said plurality of heartbeat types including said plurality of sequences of heartbeat types; and
    displaying all or a portion of selected ones of said class records.

14. The method of claim 13 wherein said method further comprises the step of forming a template for each detected heartbeat; and
    wherein the step of comparing said detected heartbeats comprises a point by point template matching comparison.

15. The method of claim 13 wherein the step of assessing the relative timing of said heartbeats comprises:
    determining the R-R interval between successive detected heartbeats;
    determining instantaneous and averaged heartrates in response to said R-R intervals; and
    comparing said instantaneous heartrate with said averaged heartrate in a predetermined manner whereby said detected heartbeats are determined to be early, regular or late.

16. The method of claim 13 wherein the step of detecting said heartbeats comprises:
    detecting candidate heartbeats;
    evaluating the noise of a portion of said ECG signal including said candidate heartbeat;
    determining whether said candidate beat is a valid, noisy or invalid heartbeat in response to said noise evaluation.

* * * * *